United States Patent [19]

Lee et al.

[11] 4,349,665

[45] Sep. 14, 1982

[54] MACROLIDE ANTIBIOTIC COMPLEX

[75] Inventors: Bong K. Lee, East Brunswick; Joseph A. Marquez, Montclair; J. Allan Waitz, Warren, all of N.J.

[73] Assignee: Schering Corporation, Kenilworth, N.J.

[21] Appl. No.: 163,461

[22] Filed: Jun. 27, 1980

[51] Int. Cl.³ ............................................ C07H 17/08
[52] U.S. Cl. .................................... 536/7.1; 424/180; 424/181; 435/76
[58] Field of Search .................................. 536/17 R, 4

[56] References Cited

U.S. PATENT DOCUMENTS 3,975,372  8/1976  Ganguly et al. ................. 536/17 R
4,092,473  5/1978  Okamoto et al. ................ 536/17 R

OTHER PUBLICATIONS

Satio et al., "The Journal of Antibiotics", vol. XXXIII, No. 4, 1980, Apr., pp. 364–376.

Primary Examiner—Johnnie R. Brown
Attorney, Agent, or Firm—Carver C. Joyner; Gerald S. Rosen; Bruce M. Eisen

[57] ABSTRACT

The AR-5-3 Complex consisting of four macrolide antibiotics is elaborated by a mutant strain of *Micromonospora polytrota*. The antibiotics exhibit substantial activity against gram positive bacteria in vitro and in vivo.

9 Claims, No Drawings

MACROLIDE ANTIBIOTIC COMPLEX

This invention relates to a novel macrolide antibiotic complex which consists of four structurally related compounds which we designated AR-5-3.

This invention also relates to the microbiological production of the complex by a mutant strain of *Micromonospora polytrota* and its use in combatting infections.

For the sake of convenience, the complex may be designated AR-5-3.

THE MICROORGANISM

The microorganism used in this invention was obtained by mutagenic treatment of *Micromonospora polytrota* ATCC 31584, NRRL 12066 by the method set forth hereinbelow. The mutant strain (SCC 1442) has been deposited with the American Type Culture Collection, Rockville, Md. (accession No. ATCC 31648), and with the Northern Regional Utilization and Research Division, AR.S, Peoria, Ill. (accession No. NRRL 12179). Sub-cultures of the mutant strain may be obtained from the above-named depositories.

When grown in a broth medium containing soluble starch and yeast extract, *M. Polytrota* SCC 1442 forms clumps of fine, 0.8 to 1.2 micron, branching mycelium. Spores are not abundantly formed even after 10 to 14 days incubation at 35° C. When present, they occur singly or in clusters along the length of the hyphae.

The organism contains meso-diaminopimelic acid (meso-DAP) as a characteristic amino acid in the cell wall. Whole cells contain arabinose and xylose as characteristic sugars.

Table 1 reports the cultural characteristic of SCC 1442 on various standard media after 14 days incubation at 30° C. (Shirling and Gottlieb, Inter. J. Syst. Bact., 16:313–340, 1966; Waksman, The Actinomycetes, Vol. II, The Williams and Wilkins Co., 1961).

The color designations assigned to the vegetative mycelial pigments consist of a color name (Descriptive Color Names Dictionary, Container Corp., America, 1950) and a color-chip number (Color Harmony Manual, ed. 4, Container Corp. America, 1958). The mutant strain is compared to the type strain, *M. polytrota* ATCC 31584.

SCC 1442 is similar to *M. polytrota* ATCC 31584 in growth, appearance, and pigmentation on most organic media. Vegetative mycelium pigmentation ranges from dark purple brown to light brown. A bloom is not formed by this strain after 14 days of incubation.

The physiologic characteristics and carbohydrate utilization of SCC 1442 are set forth in Tables 2 and 3 and are compared to ATCC 31584. The strains do not differ in the characters tested.

The characteristic difference between SCC 1442 and ATCC 31584 is in the production of antibiotics. *M. polytrota* ATCC 31584 produces the macrolide antibiotic complex described and claimed in U.S. application Ser. No. 93,080, filed Nov. 9, 1979. The same or similar antibiotics are described in British Patent publication No. 2,020,647A, published Nov. 21, 1979, now U.S. Pat. No. 4,307,085.

SCC 1442 produces a different macrolide antibiotic complex whose structures are set forth hereinbelow.

TABLE 1

Growth Characteristics of SCC 1442 compared to *M. polytrota* ATCC 31584 on Various Descriptive Media

| Medium | ATCC 31584 | SCC 1442 |
|---|---|---|
| Bennett's Agar | G: +++, good | +++, good |
|  | S: Raised, granular | Raised, folded |
|  | AM: Present; gray bloom | Absent |
|  | DFP: Present; gray-black | Absent |
|  | C: gn, charcoal | $g_4pl$, dark spice brown |
| Czapek-Sucrose Agar | G: +++, good | +++, good |
|  | S: Raised, plicate | Raised, folded |
|  | AM: Present; gray bloom | Absent |
|  | DFP: Present; dark gray | Present; faint yellow |
|  | C: gp, black | $g_4lg$, light spice brown |
| Glucose-Asparagine Agar | G: ++, moderate |  |
|  | S: Raised, granular |  |
|  | AM: Absent |  |
|  | DFP: Present; faint brown |  |
|  | C: gspo, chocolate brown |  |
| Glycerol-Asparagine Agar (ISP No. 5) | G: +, fair to poor | ±, poor |
|  | S: Granular | Non-characteristic |
|  | AM: Absent |  |
|  | DFP: Absent |  |
|  | C: $g_4lg$, light spice brown |  |
| Nutrient Agar | G: +, fair to poor | +, fair to poor |
|  | S: Granular | Flat, granular |
|  | AM: Absent | Absent |
|  | DFP: Absent | Absent |
|  | C: $g_4lg$, light spice brown | $g_4ne$, luggage tan |
| Potato-Dextrose Agar | G: ++, moderate | ++, moderate |
|  | S: Raised, plicate | Raised, plicate |
|  | AM: Present; white to gray bloom | Absent |
|  | DFP: Absent | Present; light gray |
|  | C: $g_5ml$, chocolate | $g_6nl$, dark brown |
| Emerson's Agar | G: +, fair to poor | +, fair to poor |
|  | S: Flat, granular | Flat, granular |
|  | AM: Absent | Absent |
|  | DFP: Present; gray brown | Absent |

TABLE 1-continued

Growth Characteristics of SCC 1442 compared to *M. polytrota*
ATCC 31584 on Various Descriptive Media

| Medium | ATCC 31584 | SCC 1442 |
|---|---|---|
| NZA Glucose Agar | C: g4pn, chocolate brown<br>G: +++, good<br>S: Raised, plicate<br>AM: Present; white to gray bloom<br>DFP: Absent | g4le, cedar<br>+++, good<br>Raised, plicate<br>Absent<br>Absent |
| Yeast Extract Glucose Agar | C: gn, charcoal<br>G: +++, good<br>S: Raised, plicate<br>AM: Present; white to gray bloom<br>DFP: Present; gray | g5ng, brick red<br>+++, good<br>Raised, deeply folded<br>Absent<br>Absent |
| Tomato Paste Oatmeal Agar | C: g8pn, ebony brown<br>G: +++, good<br>S: Raised, powdery<br>AM: Present; gray bloom<br>DFP: Present; faint gray | g6ng, indian red |
| Yeast Extract-Malt Extract Agar (ISP No. 2) | C: gd, gray<br>G: +++, good<br>S: Raised, plicate<br>AM: Absent<br>DFP: Present; gray | +++, good<br>raised, folded<br>Absent<br>Absent |
| Oatmeal Agar | C: g9pn, dark eggplant<br>G: +, fair to poor<br>S: Granular<br>AM: Present; white to gray bloom<br>DFP: Absent | g5pi, copper brown<br>+, fair to poor<br>Granular<br>Absent<br>Present; faint orange |
| Inorganic Salts Starch Agar | C: g5po, chocolate<br>G: ++, moderate<br>S: Flat, granular<br>AM: Present; gray bloom<br>DFP: Present; gray | g3lc, light amber<br>++, moderate<br>Flat, ribbon-like<br>Absent<br>Present; faint red |
| Starch Agar (Waksman No. 21) | C: g5po, chocolate brown<br>G: +, fair<br>S: Flat<br>AM: Present; white to gray bloom<br>DFP: Present; gray | g10po, black plum<br>+, fair<br>Flat<br>Absent<br>Present; gray-brown |
| Calcium Maleate Agar | C: g4nl, dark brown<br>G: +, fair to poor<br>S: Granular<br>AM: Absent<br>DFP: Absent | g5lg, cocoa brown<br>+, fair to poor<br>Granular<br>Absent<br>Absent |
| Tyrosine Agar (ISP No. 7) | C: g4pg, dark luggage tan<br>G: ++, moderate<br>S: Raised, plicate<br>AM: Absent<br>DFP: Present; gray brown | g3gc, light tan<br>++, moderate<br>Raised, folded<br>Absent<br>Absent |
| Starch Agar (Gordon) | C: g8pn, ebony brown<br>G: +++, good<br>S: Raised, plicate<br>AM: Present; gray bloom<br>DFP: Present; faint brown | g4lo, maple<br>++, moderate<br>Flat, furrowed<br>Absent<br>Absent |
| Gelatin Agar (McDade) | C: g10po, black plum<br>G: +, fair to poor<br>S: Granular<br>AM: Absent<br>DFP: Absent | g4ng, light brown<br>++, moderate<br>Raised, folded<br>Absent<br>Absent |
| Glucose-Asparagine Agar | C: g4nl, dark brown<br>G: +, fair<br>S: Flat, slightly folded<br>AM: Absent<br>DFP: Absent | g3ic, light amber |
| Tomato-Paste Oatmeal Agar | C: g3ca, shell<br>G: ++, moderate<br>S: Flat, slightly folded<br>AM: Absent<br>DFP: Absent | |

TABLE 1-continued

Growth Characteristics of SCC 1442 compared to *M. polytrota*
ATCC 31584 on Various Descriptive Media

| Medium | ATCC 31584 | SCC 1442 |
|---|---|---|
| | C: g5ng, brick red | |

G = growth;
S = surface characteristics;
AM = aerial mycelium;
DFP = diffusable pigments; and
C = color of the growth.

TABLE 2

Comparison of Physiologic Properties of *M. polytrota*
ATCC 31584 and SCC 1442

| Test | ATCC 31584 | SCC 1442 |
|---|---|---|
| Hydrolysis of: | | |
| Adenine | Negative | Negative |
| Hypoxanthine | Positive, strongly | Positive, strongly |
| Tyrosine | Positive, weakly | Positive, weakly |
| Casein | Positive | Positive |
| Starch | Positive | Positive |
| Gelatin | Positive | Positive |
| Xylan | Negative | Negative |
| Nitrate to Nitrate: | Weakly positive | Weakly positive |
| Growth in the Presence of: | | |
| NaCl 1.0% | +++, good | +++, good |
| 2.0% | ++, moderate | ++, moderate |
| 3.0% | +, fair to poor | +, fair to poor |
| Growth at: | | |
| 28° C. | +++, good | +++, moderate to good |
| 35° C. | +++, good | +++, good |
| 40° C. | ++, fair to moderate | ++, fair to moderate |
| 45° C. | +, fair | +, fair |
| Formation of: | | |
| H₂S | Negative | Negative |
| Melanin | Negative | Negative |

TABLE 3

Utilization of Carbohydrates

| Carbohydrate | ATCC 31584 | SCC 1442 |
|---|---|---|
| Control | Negative | Negative |
| D-Arabinose | +++, good | +++, good |
| L-Arabinose | +++, good | +++, good |
| Cellibiose | +++, good | +++, good |
| Dulcitol | −, poor | −, poor |
| Erythritol | −, poor | −, poor |
| Frucose | +++, good | +++, good |
| L-Fucose | −, poor | −, poor |
| Galactose | ±, poor to fair | ±, poor to fair |
| Glucose | +++, good | +++, good |
| α-m-d-glucoside | −, poor | −, poor |
| Glycerol | −, poor | −, poor |
| Inositol | −, poor | −, poor |
| Inulin | ±, poor to fair | ±, poor to fair |
| Lactose | −, poor | −, poor |
| Maltose | +++, good | +++, good |
| Mannitol | −, poor | −, poor |
| Mannose | +++, good | +++, good |
| Melibiose | −, poor | −, poor |
| Raffinose | −, poor | −, poor |
| Rhamnose | −, poor | −, poor |
| Ribose | +, fair | +, fair |
| Sucrose | +++, good | +++, good |
| Trehalose | +++, good | +++, good |
| D-xylose | −, poor | −, poor |

In view of the substantial similarity between *M. polytrota* ATCC 31584 and *M. polytrota* SCC 1442, the preparation of inocula, the fermentation and the nutrient media used therein are substantially identical to those set forth in application Ser. No. 93,080, filed Nov. 9, 1979, which application (now U.S. Pat. No. 4,307,085) is hereby incorporated by reference herein.

THE FERMENTATION

The fermentation is preceded by the development of a vegetative inoculum which is usually prepared in two or preferably three stages. The first stage is inoculated with a 2–10%, preferably a 2–5% by volume frozen whole broth sample of the strain which has been previously prepared. The subsequent stages are usually inoculated with from about 5 to about 10% by volume of the preceding inoculum.

The fermentation is adjusted to a pH of from about 6.5 to about 7.5, preferably at from about 6.8 to about 7.0 prior to inoculation. The temperature at which the fermentation is conducted is from about 28° to about 33° C., preferably at 30° C. with agitation. In general, the fermentation reaches peak production in about 5 to about 6 days. Monitoring of the fermentation is effected by extracting a whole broth sample with a non-water miscible organic solvent, preferably ethyl acetate, by thin layer chromatography of the extract and bioautography of the chromatogram against *Staphylococcus aureus* 209P.

ISOLATION AND PURIFICATION

When peak antibiotic production is attained, the whole broth is adjusted to pH 7.0 and extracted with ethyl acetate or other suitable non-water miscible organic solvent. The extracts are concentrated to a residue, which residue is redissolved in a minimum volume of ethyl acetate and extracted with about 2 volumes 5% acetic acid and the two liquid phases are separated. The aqueous acidic layer is adjusted to pH 8.5 and is extracted with ethyl acetate. The ethyl acetate extracts are combined, dried over sodium sulfate and concentrated to an oily residue.

SEPARATION AND PURIFICATION OF AR-5-3

The AR-5-3 Complex is separated by a High Performance Liquid Chromatography system wherein separation is effected by repetitive chromatography of fractions having substantially the same migration rate.

The HPLC System may be described as follows:
Column: ES Industries-Chromegabond C-8
Particle Size: 10 Microns
Length×I.D.: 50 cm×9.6 mm
Mobile Phase: Acetonitrile: 0.01 M ammonium acetate buffer (pH 4.0) in a ratio by volume of 40:60)
Flow Rate: 5 ml/min.
Detection: UV at 254 mm
Pressure: 1500 psi The Planar structures of the compounds of this invention were determined by physicochemical measurements such as NMR, mass spectroscopy, ultraviolet spectroscopy and the like. Also, the compounds were compared with their 3″-OCH₃ counterparts which are described and claimed in application Ser. No. 93,080 filed Nov. 9, 1979, now U.S. Pat. No. 4,307,085 and in the aforementioned British Patent Publication. Thus, the antibiotics of this invention may be depicted by the following Planar structural formulae:

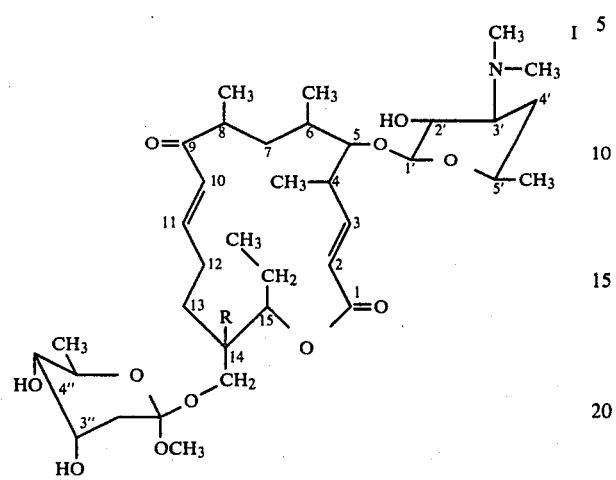

wherein R is hydrogen or hydroxy and the dotted line represents a double bond between the carbon atoms of positions 12 and 13 or together with the carbon atoms at positions 12 and 13 an oxirane ring.

The individual members of the Complex may be depicted by the following Planar structural formulae:

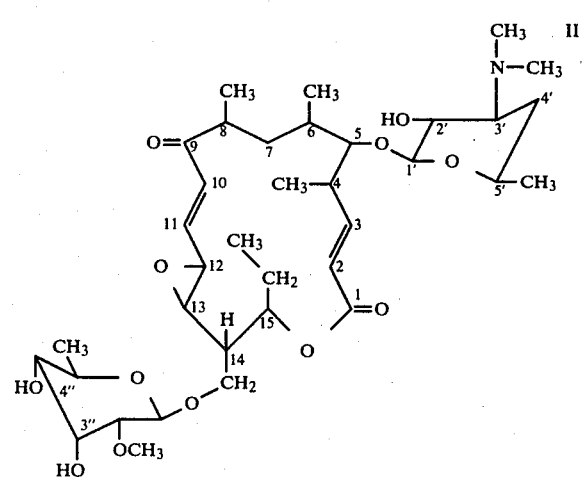

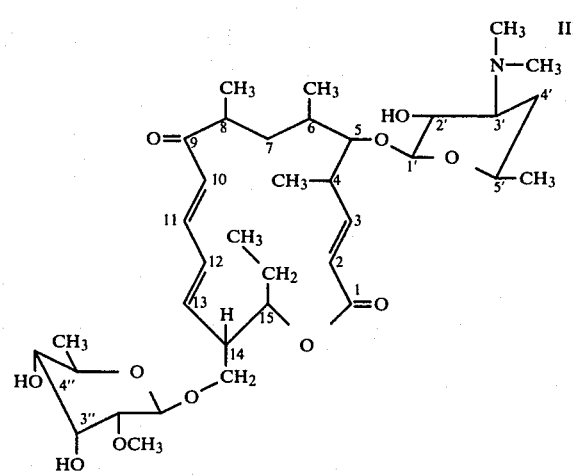

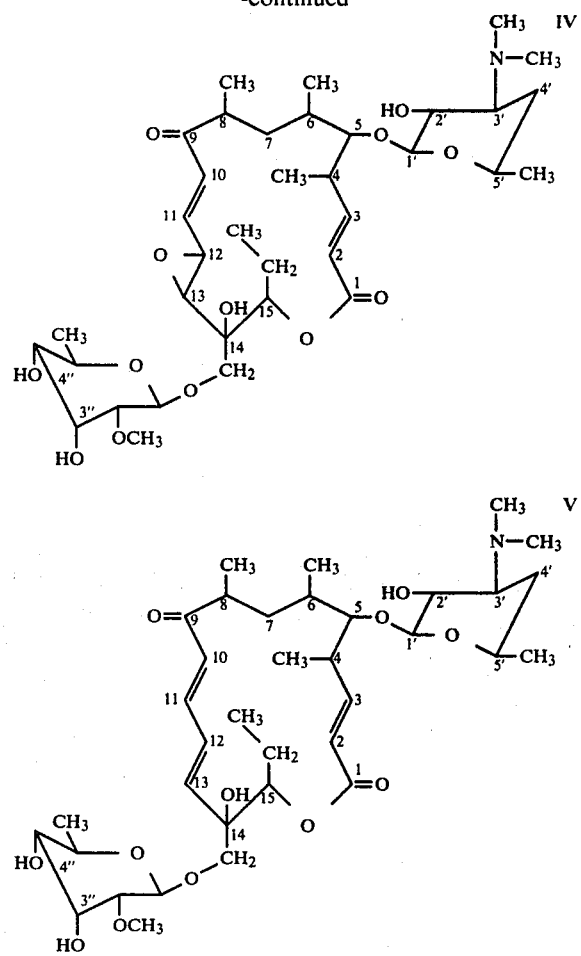

The antibiotics of this invention are capable of forming non-toxic pharmaceutically acceptable acid addition salts by virtue of the dimethylamino group at position 3. By non-toxic pharmaceutically acceptable acid addition salts is meant those that do not exhibit toxic manifestations at normal therapeutic doses.

In view of their close structural relationship with the compounds of application Ser. No. 93,080, we have given the compounds of this invention the following trivial names:

Compound II—3''-desmethyl AR-5-1,

Compound III—3''-desmethyl-12,13-desepoxy-12,13-dehydro AR-5-1,

Compound IV—3''-desmethyl AR-5-2, and

Compound V—3''-desmethyl-12,13-desepoxy-12,13-dehydro AR-5-2.

Exemplary of such salts are those formed with such acids as hydrochloric, sulfuric, phosphoric, citric acetic, propionic, tartaric, maleic, benzoic, cyclopropylcarboxylic, adamantyl carboxylic and the like. Acid addition salts may be prepared by methods generally used in the art, such as by adding a stoichiometric amount of acid to a solution of antibiotic in a non-reactive organic solvent and isolating the salt by methods known in the art such as precipitation with a solvent wherein the salt is not appreciably soluble, e.g. diethyl ether, hexane. A non-reactive solvent is one which does not react with the antibiotic, the acid or the salt.

The hydroxyl groups at positions 2', 3" and 4" are amenable to esterification to form non-toxic pharmaceutically acceptable esters, such as, for example, those formed by reaction with typical acylating agents such as with anhydrides or chlorides of organic acids, especially hydrocarbon carboxylic acids. Further, the antibiotics of this invention are susceptible to the formation of 2'-monoesters, 2',3",4"-triesters, and, by selective solvolysis of the 2'-ester, 3", 4"-diesters may be obtained.

In vitro activity of the AR-5-3 Complex

The in vitro Minimal Inhibitory Concentration of the AR-5-3 Complex was obtained using Mueller-Hinton Agar with 5% sheep blood. The results are reported in micrograms per ml.

| AR-5-3 Activity Against Staphylococcus | |
|---|---|
| Organism | MIC |
| Staphylococcus | .25 |
| Staphylococcus AF-1 | .25 |
| Staphylococcus Giorgio | .25 |
| Staphylococcus Gray | .25 |
| Staphylococcus Wood | .25 |
| Staphylococcus Ziegler | .25 |
| Staphylococcus 59N | .25 |
| Staphylococcus 168 | .125 |
| Staphylococcus 209P | .125 |
| Staphylococcus 306 | .25 |
| Staphylococcus 676 | .25 |
| Staphylococcus 1613 | .5 |
| Staphylococcus 76083002 | .125 |
| Staphylococcus 76050601 | .125 |
| Erythromycin Resistant | |
| Staphylococcus 76080401 | >16 |
| Staphylococcus 76070105 | >16 |
| Staphylococcus 76070106 | 2 |
| Staphylococcus 76070108 | .125 |
| Macrolide Resistant | |
| Staphylococcus 76010501 | >16 |
| Staphylococcus 76061501 | >16 |
| Staphylococcus 76070103 | >16 |
| Staphylococcus ATCC 27626 | >16 |

| AR-5-3 Activity Against Streptococcus | | |
|---|---|---|
| Organism | Group | MIC |
| 5140 | A | 2 |
| G-F | A | .25 |
| Y | A | 2 |
| Harper | A | 16 |
| ATCC 191615 | A | .25 |
| Divesta | A | 8 |
| Murc | C | .25 |
| Thacker | C | >16 |
| M-6 | C | >16 |
| Parsons | G | .25 |
| Hamer | G | 16 |
| Lang | B | 16 |
| Crisp | B | >16 |
| Petruzzlio | B | >16 |
| G-B | B | >16 |
| G-D | B | >16 |
| G-G | B | >16 |
| | *Streptococcus* | |
| Jameson | pneumoniae | 2 |
| Schmitt | " | 2 |
| X | " | 8 |
| M-2 | " | 16 |
| Bloom | " | 16 |
| Haskins | " | 16 |
| Lutte | viridans | >16 |
| 1578 | " | >16 |
| 1141 | " | >16 |
| 1626 | " | >16 |
| 1142 | " | >16 |
| 1022 | D non-enterococcus | >16 |
| 0969/72 | D non-enterococcus | >16 |
| Getz | D enterococcus | >16 |
| McCormick | D enterococcus | >16 |
| Z | D enterococcus | >16 |
| M-3 | D enterococcus | >16 |
| Wd | D enterococcus | >16 |
| Q | D enterococcus | >16 |

Oral administration of 2 mg of approximately a 50:50 mixture of compounds IV and V to Carworth Farms CF1 mice gave serum levels of 0.73 micrograms/ml in one-half hour and of 10.07 micrograms per ml in one hour. Based upon the MIC data, it is evident that in one hour a therapeutic level of antibiotic for treating infections by a host of organisms, especially gram positive organisms, is already in the serum.

By virtue of their in vivo activity the antibiotics of this invention may be administered topically, parenterally and orally, preferably in admixture with suitable pharmaceutically acceptable excipients and diluents. These antibiotics may be administered in the form of non-toxic pharmaceutically acceptable esters or in the form of non-toxic pharmaceutically acceptable acid addition salts.

The dosage forms, excluding topicals should be designed to permit the administration of from about 5 to about 50 mg per kg per day preferably in divided dosages to be administered 2 to 4 times per day. Topical formulations should also be applied to the affected areas 2 to 4 times a day and should contain from about 5 to about 15, preferably about 10 grams per liter for lotions and the same quantity per kilogram for ointments.

THE MUTATION

*Micromonospora polytrota* ATCC 31648, NRRL 12179 was prepared by a double mutation, the first of which was performed upon *M. polytrota*, ATCC 31584, NRRL 12066. The intermediate mutant (GS-Ml-7101) was isolated and subjected to a second mutagenic treatment. Each mutation was performed according to the following procedure:

Three ml of a frozen cell preparation are inoculated into 50 ml of sterile Medium No. 1 in a 250 ml shake flask and the flask is shaken at 350 r.p.m at 30° C. for 72 hours. Ten ml of the culture medium is centrifuged, resuspended in 20 ml of 0.05 M[mono-tris(hydroxymethyl)aminomethane maleate]buffer PH 6.0; hereafter Tris-buffer, and sonicated for 30 minutes in an ice bath. The suspension is centrifuged, the sediment is resuspended in 29 ml of Tris-buffer, sonicated again for 30 minutes in an ice bath and N-Methyl-N'-nitro-N-Nitroso-guanidine (NTG) is added to a concentration of 200 micrograms per ml. The mixture is shaken at 250 r.p.m. for 30 to 120 minutes at 30° C. and 1.0 ml samples are withdrawn at 30 minute intervals. Nine (9) ml of Tris-buffer is added to each sample and the suspension is centrifuged at 250 r.p.m. The sediment is again resuspended in 10 ml of Medium No. 1 and shaken for 180 minutes at 30° C., sonicated for 15 minutes in an ice bath and diluted to $10^{-7}$ with distilled water. The diluted samples are plated on Medium No. 2 (agar) and incubated for 10 to 14 days at 30° C. Colonies are picked at random and the colony which appears to be healthiest (more profuse growth) is selected for a second mutagenic treatment which is performed exactly as the first.

After the second mutagenic treatment, the colony having the healthiest appearance is again selected and grown on Medium No. 1 for 72 hours at 30° C. Sixtenths (0.6) ml of the whole broth is transferred into 10 mls of Medium No. 3 and incubated for 5 days at 30° C. The whole broth is harvested by extraction twice with 20 ml of ethyl acetate. The extracts are combined, concentrated to dryness and redissolved in 0.3 ml of a mixture of chloroform-methanol (1:1 by volume). Five microliters of the solution is spotted on Whatman LK6DF plates and the chromatogram is developed using the lower phase of a chloroform-methanol −17% ammonium hydroxide (40:12:20) solvent system. The developed plates are bioautographed against Staph. aureus 6358P. The compounds of this invention have $R_f$ values of 0.41 and 0.27.

| MEDIA | |
|---|---|
| (a) No. 1 | |
| Beef Extract | 3.0 gms. |
| Tryptone | 5.0 gms. |
| Yeast Extract | 5.0 gms. |
| Cerelose | 1.0 gms. |
| Potato Starch | 24.0 gms. |
| CaCO3 | 2.0 gms. |
| Anti-foam | 1 ml |
| Tap H2O | 1000 ml |
| Adjust pH to 7.5 | |
| (b) No. 2 | |
| Beef Extract | 3.0 gms. |
| Tryptone | 5.0 gms. |
| Yeast Extract | 5.0 gms. |
| Cerelose | 1.0 gms. |
| Soluble Starch | 24.0 gms. |
| CaCO3 | 2.0 gms. |
| Agar | 15.0 gms. |
| Tap H2O | 1000 ml. |
| Anti-foam | 2.0 ml |
| Adjust pH to 7.5 | |
| (c) No. 3 | |
| J-Starch | 50.0 gms. |
| Distillers Solubles | 7.5 gms. |
| Pharmamedia | 5.0 gms. |
| Tap H2O | 1000 ml |
| Anti-Foam | 1 ml |
| Adjust pH to 7.0 | |

We claim:

1. AR-5-3 Complex consisting of compounds having the Planar structural formula:

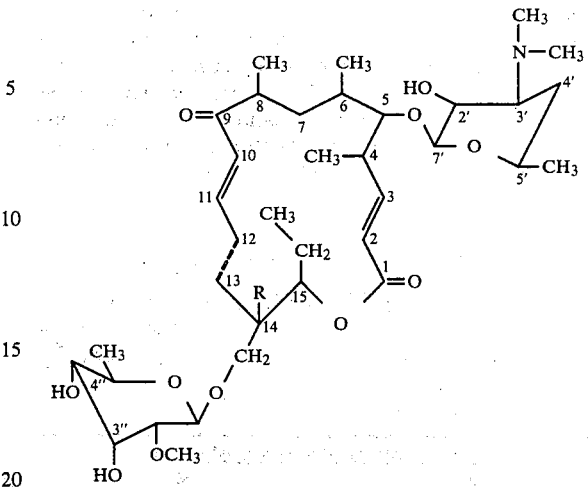

wherein R is hydrogen or hydroxy and the dotted line represents a double bond between the carbon atoms of positions 12 and 13 or together with the carbon atoms at positions 12 and 13 an oxirane ring and the non-toxic pharmaceutically acceptable acid addition salts, and the non-toxic pharmaceutically acceptable 2'-monoesters, the 3'',4''-diesters, and the 2',3'',4'' triesters thereof, wherein the acyl moiety of said esters are derived from hydrocarbon carboxylic acids having 2 to 18 carbon atoms, and R is a member of the group consisting of hydrogen and hydroxy.

2. A composition having substantial antibiotic activity, said composition consisting essentially of a mixture of 3''-desmethyl AR-5-1, 3''-desmethyl 12,13-desepoxy-12,13-dehydro AR-5-1, 3''-desmethyl AR-5-2 and 3''-desmethyl-12,13-desepoxy-12,13-dehydro AR-5-2.

3. A composition of claim 2 having substantial antibiotic activity, said composition consisting essentially of a mixture of 3''-desmethyl-AR-5-2 and 3''-desmethyl-12,13-desepoxy-12,13-dehydro-AR-5-2.

4. A composition of claim 2 having substantial antibiotic activity, said composition consisting essentially of a mixture of 3''-desmethyl-AR-5-1 and 3''-desmethyl-12,13-desepoxy-12,13-dehydro AR-5-1.

5. A non-toxic pharmaceutically acceptable 2'-monoester of a compound of claim 2.

6. A non-toxic pharmaceutically acceptable acid addition salt of a compound of claim 3.

7. The compound of claim 1 wherein R is hydrogen and the dotted line between positions 12 and 13 in the formula represents an oxirane ring, said compound being 3''-desmethyl-AR-5-1.

8. The compound of claim 1 wherein R is hydroxy and the dotted line between positions 12 and 13 in the formula represents an oxirane ring, said compound being 3''-desmethyl-AR-5-2.

9. The compound of claim 1 wherein R is hydroxy and the dotted line between positions 12 and 13 in the formula represents a double bond, said compound being 3''-desmethyl-12,13-desepoxy-12,13-dehydro-AR-5-2.

* * * * *